US00PP13913P39

(12) United States Plant Patent
Fleming et al.

(10) Patent No.: US PP13,913 P3
(45) Date of Patent: Jun. 24, 2003

(54) HIBISCUS PLANT NAMED 'TORCHY'

(76) Inventors: David W. Fleming, 8101 S. 14th St., Lincoln, NE (US) 68512; Gretchen A. Zwetzig, 8101 S. 14th St., Lincoln, NE (US) 68512

( * ) Notice: Subject to any disclaimer, the term of this patent is extended or adjusted under 35 U.S.C. 154(b) by 17 days.

(21) Appl. No.: 09/950,212

(22) Filed: Sep. 10, 2001

(65) Prior Publication Data

US 2003/0051283 P1 Mar. 13, 2003

(51) Int. Cl.[7] ..... A01H 5/00

(52) U.S. Cl. ..... Plt./257

(58) Field of Search ..... Plt./257, 266

*Primary Examiner*—Bruce R. Campell
*Assistant Examiner*—June Hwu

(57) ABSTRACT

A new and distinct cultivar of winter hardy Hibiscus plant named, 'Torchy' is the result of a unique hybridization. This new and distinct cultivar is characterized primarily as to novelty by its extreme cold hardiness to Zone 4, its bright green, deeply-lobed leaves, its large, campanulate, red flowers with ruffled petal edged, its vigorous and uniform growth habit, and its floriferous nature from midsummer until frost.

2 Drawing Sheets

LATIN NAME OF THE GENUS AND SPECIES OF THE PLANT CLAIMED

Hibiscus hybrid.

VARIETY DENOMINATION

'Torchy'.

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined and uniquely colored 3-lobed leaves which are severaly cut with slightly serrated margins and some entire margins along the sinuses and the leaves have a bright green color that compliments the landscape;

(b) Shimmering dark red buds that open into large ruffled flowers that are well-posed on the plant and outstanding for their medium-to dark red, thick-textured petals rich in effect;

(c) The plant being very floriferous with flowers that stay open at least one full day;

(d) The plant being medium-sized, but vigorous, with compact and uniform breaking action which gives it unique landscape utility; and (e) The plant being so hardy that it can consistently withstand winter temperatures of at least −30 degrees Fahrenheit.

SUMMARY OF THE INVENTION

'Torchy' a *Hibiscus moscheutos* was the result of a 40-year breeding program. Its ancestry includes *Hibiscus Militaris* (nonpatented, *Hibiscus moscheutos* (nonpatented), and *Hibiscus coccineus* (nonpatented). More specifically, the plant resulted from a selected seedling of the Fleming 'Avalon' hybrids (nonpatented), which included crosses between the above-mentioned species. The seedling which most nearly met all above named standards was selected.

This new plant first bloomed in the summer of 1978 and was selected by David Fleming and Gretchen Zwetzig on David Fleming's property in Lincoln, Nebr. The plant was observed here under typical conditions for NE, at approximately 3 years of age. Asexual propagation of the plant by cuttings and root division in Lincoln, Nebr., has shown that the unique and distinguishing features of the plant are faithfully transmitted from generation to generation and appear to be fixed.

Since its origin, the plant has bloomed from midsummer until frost, while exhibiting the above-mentioned distinctive characteristics. This hardy hibiscus plant contributes to the market with its shear beauty, its compact Growth habit, its great resistance to disease and insects, its stability through extremes in rain and drought, and its Extreme hardiness.

BRIEF DESCRIPTION OF THE DRAWINGS

The flower, bud, foliage, and growth habit of the plant are shown in the attached illustrations.

More specifically, Sheet 1 shows a close-up of the bloom and foliage.

Sheet 2 shows a close-up of the foliage and the growth habit of The cultivar, from the ground up to the apex of the plant. The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE and number designations are in accordance with the *Dictionary of Color* (*Maers and Paul*) , while general color recitations are consistent with ordinary American color terminology.

'Torchy' as not been observed under all possible environmental conditions. It is to be understood that the phenotype may vary significantly with variations in environment such as temperature, light intensity, and day length, without, however any difference in genotype of the plant. The following botanical characteristics and observations are taken from the plant when grown under normal outdoors conditions in Lincoln, Nebr.

THE PLANT

Parentage:

*Seed Parent.*—*Hibiscus militaris*×*Hibiscus coccineus*×*Hibiscus moscheutos,* 'Avalon', an unpatented Fleming seedling.

*Pollen parent.*—*Hibiscus militaris*×*Hibiscus coccineus*×*Hibiscus moscheutos,* 'Avalon', an unpatented Fleming seedling.

Origin: A selected seedling from stated crosses.

Type of plant: Hardy herbaceous perennial.

Classification: Hybrid Hibiscus plant.

Propagation: Relatively easy to propagate; holds its distinguishing characteristics through successive propagations by cuttings and division.

Size: About 3 feet, 3 inches tall; about 2 feet, 6 inches wide.

Form: Symmetrical annual growth from perennial roots.

Habit: Upright and uniformly branched.

Growth: Vigorous; medium and compact, Full-grown (3½' ) in two years.

Hardiness: Hardy to at least −30 degrees Fahrenheit.

General health: Plant is very disease resistant to rot, aphids, spidermites, scale, whitefly, etc. They are sturdy through excessive drought or water.

Propagations: Relatively easy; fast rooting.

Foliage:

1. *Arrangement.*—Alternate.
2. *Shape.*—Juvenile-variable, 3-lobed, deeply-cut leaf with margins having some serrations with entire margin along the sinuses, acute apices, rounded base-shape.
3. *Size.* —Mature leaf — (petiole base to apex) length is about 8½ inches (21.5 cm), width is about 8 inches (21 cm), rounded base-shape.
4. *Color.*—Young leaves — (upper side) — 6-L, page 67, PLATE 22. Mature leaves — (upper side) — 5-L, page 69, PLATE 23. Veins — Slightly darker than 5-L, page 69, PLATE 23. Underside of leaves — 4-E, page 67, PLATE 22.
5. *Surface texture.*—Glabrous (to very glabrous on lower leaves).
6. *Petiole length.*—About 1¾ inches (4.5 cm).
7. *Petiole color.*—Green; 5-L, page 53, PLATE 15; Pink: 1-H, page 53, PLATE 15.

Stems: The stems are stout at the base, becoming more slender toward the apices; Green: 5-L, page 53, PLATE 15; Pink: 1-H, page 53, PLATE 15.

Blooming period: Profuse from July until frost. Average number of blooms per plant: 10–25 daily; approximately 600 per season.

Flower diameter: Large; about 7¼ inches (18.5 cm).

Borne: Singly in leaf axils, from midpoint of stems upward.

Bloom duration: Individual bloom lasts at least one full day.

Form: Campanulate; petals are also very overlapping and ruffled.

Bud:

1. *Length.*—About 1¾ inches (4.5 cm), on day before opening.
2. *Color.*—12-A, page 135, PLATE 56.
3. *Surface texture.*—Glabrous.
4. *Duration.*—1 to 2 weeks.

Corolla:

1. *Petal character and dimensions.*—Campanulate, very overlapping and ruffled. Length: About 3½ inches (9.5 cm). Width: About 4¾ inches (12.5 cm).
2. *Coloration.*—Medium red with an eye of equivalent color, except for base of petals having white coloring. (about 2 inches, 5 cm). (a) Red petals — 6-C, page 37, PLATE 7; Base of petals — White: 1-A, page 25, PLATE 1. (b) Venation in petals — 12-C, page 135, PLATE 56. (c) Eye zone —12-C, page 135, PLATE 56.
3. *Texture.*—Smooth.
4. *Substance.*—Thick.
5. *Shape.*—Campanulate, very overlapping and ruffled.

Reproductive organs:

1. *Staminal column.*—Stamen along basal two-thirds. Stamen length — About 2½ inches (5.5 cm). Stamen color — 3-G, page 29, PLATE 3. Pollen color — 2-L, page 43, PLATE 10.
2. *Style.*—Terminates upper one-third of staminal column. Stigmatic lobe color — 7-A, page 43, PLATE 10. Calyx: Connate at the base; about 1½ inches (3 cm) in length. Stipules: None. Epicalyx: Whorl of bracts. 1. Shape: 7–10 slender, sword shaped bractlets. 2. Length: About 1⅜ inches (3.5 cm). 3. Color: 6-K, page 67, PLATE 22. Peduncle: 1. Length: About 3¾ inches (9.5cm). 2. Strength: Stiff and sturdy. 3. Color: 3-L, page 53, PLATE 15 Seeds: 1 cm. Diameter: 1 cm. 2. Shape: Round. 3. Color: Brown: 8-A, page 33, PLATE 15.

GENERAL OBSERVATIONS

This plant, as a hybridized hardy Hibiscus, is valuable to the landscape market for its improvements in thicker-textured and uniquely colored and shaped flowers, refined, deeply-lobed light green leaves, all-around vigor, good breaking action, and adaptation to extreme environments, including the ability to consistently survive winter temperatures of at least−30 degrees Fahrenheit.

We claim:

1. A new and distinct cultivar of Hibiscus plant, as herein shown and described, characterized by its bright green, refined and deeply lobed foliage, its large, overlapping velvety red flowers with ruffling at the petal edges, its more compact size, its vigor, and its hardiness.

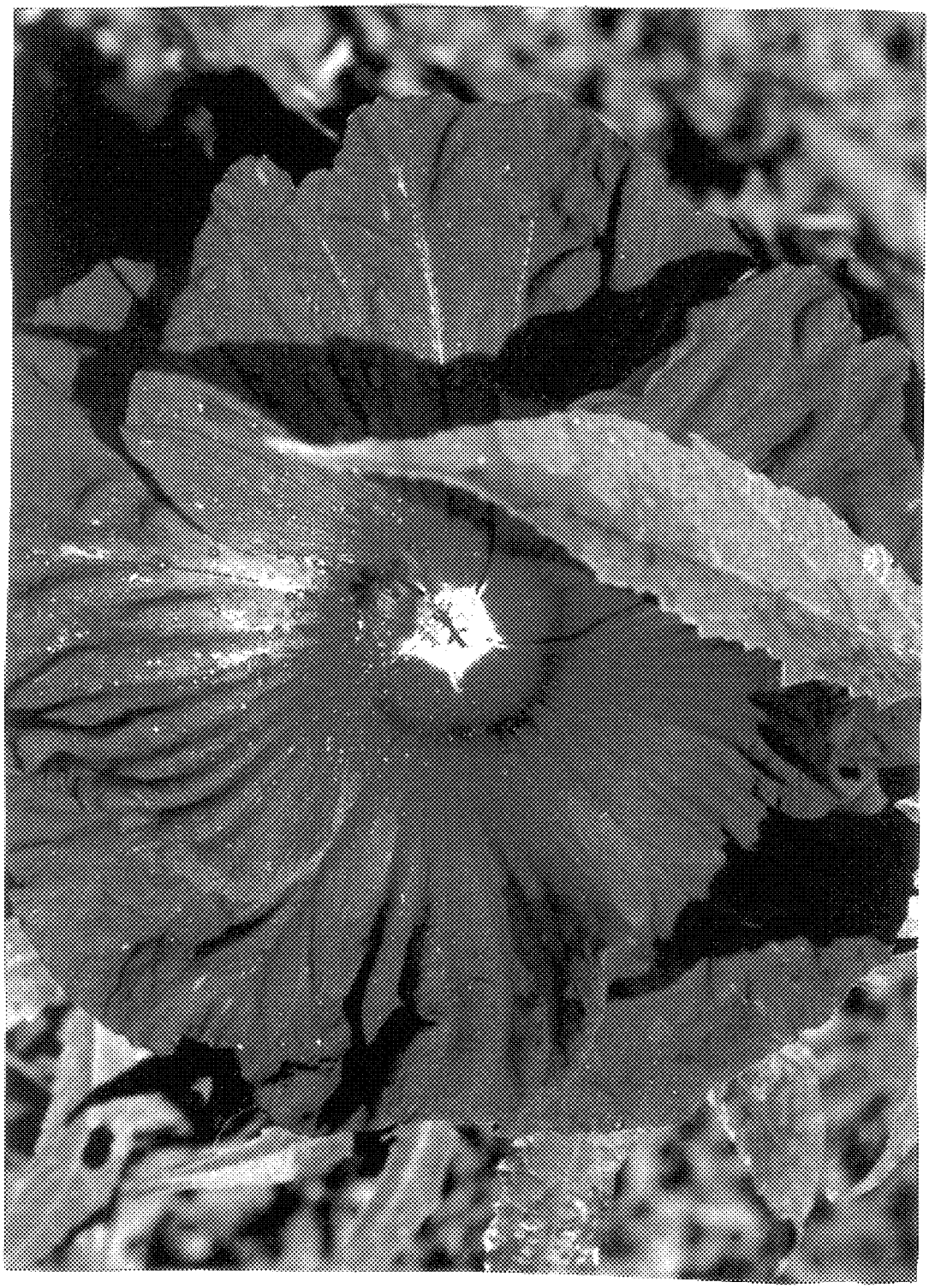

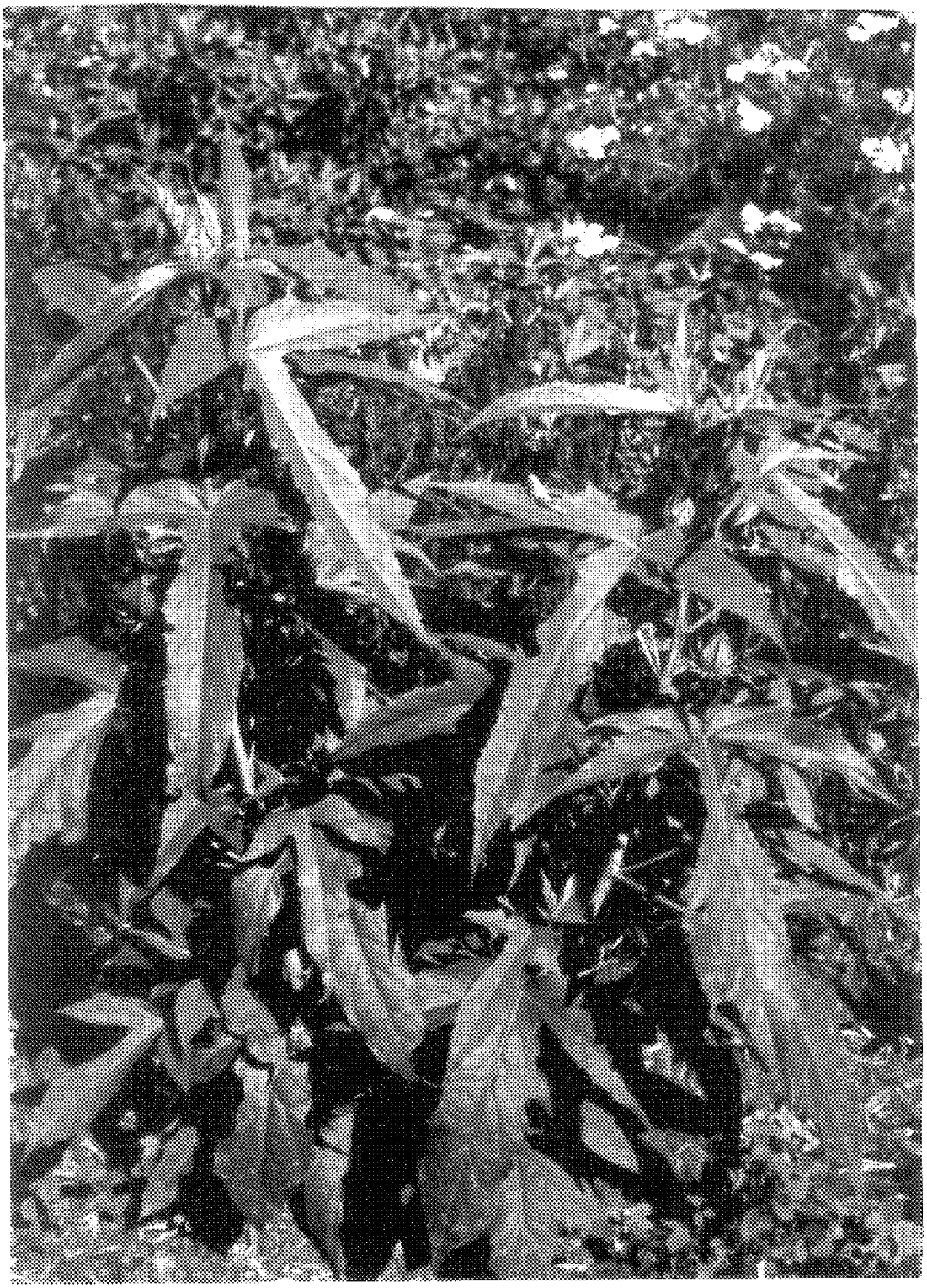

* * * * *